(12) United States Patent
Sagues et al.

(10) Patent No.: US 11,448,610 B2
(45) Date of Patent: Sep. 20, 2022

(54) SYSTEM AND METHOD FOR IMAGING TENDON CROSS SECTIONS FOR DETECTING VOIDS AND OTHER DEFICIENCIES IN GROUTED EXTERNAL TENDONS

(71) Applicant: UNIVERSITY OF SOUTH FLORIDA, Tampa, FL (US)

(72) Inventors: Alberto A. Sagues, Lutz, FL (US); Hani Freij, Tampa, FL (US); David Adam Dukeman, New Port Richey, FL (US); Christopher Lewis Alexander, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 17/626,658

(22) PCT Filed: Jul. 10, 2020

(86) PCT No.: PCT/US2020/041659
§ 371 (c)(1),
(2) Date: Jan. 12, 2022

(87) PCT Pub. No.: WO2021/011396
PCT Pub. Date: Jan. 21, 2021

(65) Prior Publication Data
US 2022/0214294 A1 Jul. 7, 2022

Related U.S. Application Data

(60) Provisional application No. 62/873,369, filed on Jul. 12, 2019.

(51) Int. Cl.
*G01N 27/82* (2006.01)
*G01N 27/20* (2006.01)
(Continued)

(52) U.S. Cl.
CPC ............ *G01N 27/20* (2013.01); *G01N 27/82* (2013.01); *G01N 27/902* (2013.01);
(Continued)

(58) Field of Classification Search
CPC ...... G01N 27/20; G01N 33/383; G01N 27/82; G01N 27/902; G01N 27/9046;
(Continued)

(56) References Cited

U.S. PATENT DOCUMENTS

| 5,420,589 A | 5/1995 | Wells et al. |
|---|---|---|
| 9,535,026 B2 | 1/2017 | Marashdeh et al. |

(Continued)

OTHER PUBLICATIONS

Azizinamini et al., Improved Inspection Techniques for Steel Prestressing/Post-Tensioning Strand, FDOT Contract No. BDK80 977-13, Final Report—vol. I, Jun. 2012, 111 pages.

(Continued)

*Primary Examiner* — Raul J Rios Russo
(74) *Attorney, Agent, or Firm* — Quarles & Brady LLP

(57) ABSTRACT

An exemplary method of indicating a condition of grout within a post-tensioned tendon involves positioning a magnet and a metallic sensing plate in close proximity to an outer surface of the post-tensioned tendon; rotating the magnet and the metallic sensing plate around the outer surface of the post-tensioned tendon; measuring an amount of magnetic forces applied to the magnet during rotation of the magnet around the post-tensioned tendon; measuring an impedance between the metallic sensing plate and metallic strands within the post-tensioned tendon during rotation of the metallic sensing plate around the post-tensioned tendon; and generating an image of a cross-section of the post-tensioned tendon indicating one or more grout conditions in spatial proximity to the metallic strands within the post- (Continued)

tensioned tendon based on measurement data using the magnet and the metallic sensing plate.

20 Claims, 5 Drawing Sheets

(51) Int. Cl.
    *G01N 33/38*     (2006.01)
    *G01N 27/9013*     (2021.01)
    *G01N 27/90*     (2021.01)
    *E04C 5/10*     (2006.01)
    *G01R 33/12*     (2006.01)
    *G01R 33/10*     (2006.01)
    *G01R 33/028*     (2006.01)

(52) U.S. Cl.
    CPC ..... *G01N 27/9006* (2013.01); *G01N 27/9046* (2013.01); *G01N 33/383* (2013.01); *E04C 5/10* (2013.01); *G01R 33/028* (2013.01); *G01R 33/10* (2013.01); *G01R 33/12* (2013.01)

(58) Field of Classification Search
    CPC ...... G01N 27/9006; E04C 5/10; G01R 33/12; G01R 33/10; G01R 33/028; G01R 33/093
    USPC .................... 324/51, 55, 200, 228, 239, 240
    See application file for complete search history.

(56) References Cited

U.S. PATENT DOCUMENTS

| | | | |
|---|---|---|---|
| 9,651,357 B1 | 5/2017 | Sagüés | |
| 10,012,615 B1 | 7/2018 | Mergelas | |
| 2015/0097589 A1* | 4/2015 | Orazem | G01N 17/04 324/693 |
| 2016/0025680 A1* | 1/2016 | Schein, Jr. | G01N 27/82 324/228 |
| 2016/0161436 A1* | 6/2016 | Marashdeh | G01N 27/226 324/681 |
| 2017/0269014 A1 | 9/2017 | Togaru | |

OTHER PUBLICATIONS

Azizinamini et al., FDOT Protocol for Condition Assessment of Steel Strands in Post-Tensioned Segmental Concrete Bridges, FDOT Contract No. BDK80 977-13, Final Report—vol. II, Jun. 2012, 25 pages.
Cabeza et al., Impedance Spectroscopy to Characterize the Pore Structure During the Hardening Process of Portland Cement Paste, Electrochimica Acta, 2006, 51(8-9):1831-1841.
Corven Engineering, Inc., Final Report—Mid-Bay Bridge Post-Tensioning Evaluation (Florida Department of Transportation District 3), Oct. 10, 2001, 68 pages.
Davis, Using Small, Rare-Earth Magnets to Study the Susceptibility of Feebly Magnetic Metals, American Journal of Physics, 1992, 60(4):365-370.
Dugarte et al., Accounting for Temperature Effects on an Evolving Galvanic Anode Cathodic Protection System for Steel in Concrete, Corrosion, 2016, 72(11):1462-1469.
Dughaish, Variation of the Dielectric Properties of Low Density Polyethylene (LDPE) with Heat Treatments and UV-irradiation, Journal of Natural Sciences and Mathematics, 2012, 6(1):63-73.
Dukeman et al., Final Report—Field Demonstration of Tendon Imaging Methods, Contract No. BDV25-977-52, Jul. 2019, 48 pages.
Duncan et al., Ultrasonic NDT Prototype for the Inspection of Ducted Post Stressing Tendons in Concrete Beams, In Review of Progress in Quantitative Nondestructive Evaluation, 1996, vol. 15, pp. 1799-1806.

Elsener et al., Quality Control and Monitoring of Electrically Isolated Post-Tensioning Tendons in Bridges, Eidgenössisches Departement für Umwelt, Verkehr, Energie und Kommunikation UVEK, Bundesamt für Strassen 647, 2011, 54 pages.
Euclid Chemical, Euco Cable Grout PTX—High Performance Cable Grout—Product Information—First Accessed Jul. 2, 2018, 2 pages.
Fernandes et al., Field Test of Magnetic Methods for Corrosion Detection in Prestressing Strands in Adjacent Box-Beam Bridges, Journal of Bridge Engineering, 2012, 17(6):984-988.
Grove et al., Determining Dielectric Constants Using a Parallel Plate Capacitor, American Journal of Physics, 2005, 73(1):52-56.
Hallaji et al., Electrical Impedance Tomography-Based Sensing Skin for Quantitative Imaging of Damage in Concrete, Smart Materials and Structures, 2014, 23(8):085001, pp. 1-13.
Hurlebaus et al., Condition Assessment of Bridge Post-Tensioning and Stay Cable Systems Using NDE Methods, Final Report Prepared for NCHRP, Project No. 14-28, Sep. 2016, 810 pages.
Im et al., Inspection of Voids in External Tendons of Posttensioned Bridges, Transportation Research Record, 2010, 2172(1):115-122.
Im et al., Non-Destructive Testing Methods to Identify Voids in External Post-Tensioned Tendons, KSCE Journal of Civil Engineering, 2012, 16(3):388-397.
Iyer et al., Ultrasonic Imaging—A Novel Way to Investigate Corrosion Status in Post-Tensioned Concrete Members, Journal of the Indian Institute of Science, 2002, 82(5 & 6):197-217.
Klein et al., Contact Potential Differences Measurement: Short History and Experimental Setup for Classroom Demonstration, IEEE Transactions on Education, 2003, 46(3):338-344.
Kranc et al., Polarization Current Distribution and Electrochemical Impedance Response of Reinforced Concrete When Using Guard Ring Electrodes, Electrochimica Acta, 1993, 38(14):2055-2061.
Krause et al., Ultrasonic Imaging Methods for Investigation of Post-Tensioned Concrete Structures: A Study of Interfaces at Artificial Grouting Faults and Its Verification, Journal of Nondestructive Evaluation, 2008, 27(1):67-82.
Lampinen et al., Application of Bayesian Neural Network in Electrical Impedance Tomography, In IJCNN'99 International Joint Conference on Neural Networks Proceedings (Cat. No. 99CH36339), IEEE, 1999, vol. 6, pp. 3942-3947.
Liu et al., An Overview of Corrosion Damage Detection in Steel Bridge Strands Using TDR, In Proc. of the 2nd International Symposium on TDR for Innovative Applications, Evanston, Ill.: Northwestern University, 2001, 12 pages.
Mariscotti et al., Gamma-ray Imaging for Void and Corrosion Assessment in PT Girders, NDE/NDT for Highways and Bridges-Structural Materials Technology (SMT), 2008, pp. 1-14.
Mariscotti et al., Gamma-ray Imaging for Void and Corrosion Assessment, Concrete International, 2009, 31(11):48-53.
Mariscotti et al., Determination of Grouting Defects in "Deep" PT Ducts Using Gamma Rays, Structural Materials Technology, 2014, 1 page.
Milovanovic et al., Review of Active IR Thermography for Detection and Characterization of Defects in Reinforced Concrete, Journal of Imaging, 2016, 2(2):1-27.
Morris et al., Practical Evaluation of Resistivity of Concrete in Test Cylinders using a Wenner Array Probe, Cement and Concrete Research, 1996, 26(12):1779-1787.
Pollock et al., Detection of Voids in Prestressed Concrete Bridges Using Thermal Imaging and Ground-Penetrating Radar, Washington State Transportation Center (TRAC), Report No. WA-RD 717.1, Dec. 2008, 77 pages.
Presuel-Moreno et al., Bulk Magnetic Susceptibility Measurements for Determination of Fly Ash Presence in Concrete, Cement and Concrete Research, 2009, 39(2):95-101.
Ru et al., Neural Networks in Electrical Capacitance Tomography (ECT)-Based Interface Detection, Measurement Science and Technology, 2011, 22(10):104006, 14 pages.
Sagues et al., Vibrational Tension Measurement of External Tendons in Segmental Posttensioned Bridges, Journal of Bridge Engineering, 2006, 11(5):582-589.

(56) References Cited

OTHER PUBLICATIONS

Sagues et al., Kelvin Probe Electrode for Contactless Potential Measurement on Concrete—Properties and Corrosion Profiling Application, Corrosion Science, 2012, 56:26-35.
Soutsos et al., Dielectric Properties of Concrete and Their Influence on Radar Testing, NDT&E International, 2001, 34(6):419-425.
Taveira et al., Early Warning Corrosion Detection in Post Tensioned Tendons, Contract No. BD544-08, Final Report to Florida Department of Transportation, Oct. 31, 2007, 72 pages.
Taveira et al., Electrochemical Noise Corrosion Monitoring of Post Tensioned Tendons, 210th ECS Meeting, 2006, Abstract #830, 1 page.
Taveira et al., Detection of Corrosion of Post-Tensioned Strands in Grouted Assemblies, Nace International Corrosion 2008 Conference & Expo, Paper No. 08398, pp. 1-19.
Terzioglu et al., Nondestructive Evaluation of External Post-Tensioning Systems to Detect Grout Defects, J. Struct. Eng., 2019, 145(1):05018002, pp. 1-15.
Thaler, Maintaining Our Infrastructure With TendonScan(R) Post Tension Tendon Inspection Service, Infrastructure Preservation Corporation, Aug. 1, 2018, https://www.infrastructurepc.com/maintaining-our-infrastructure-with-tendonscan-post-tension-tendon-inspection-service/, 10 pages.
Yang, Modelling of Capacitance Tomography Sensors, IEE Proceedings—Science, Measurement and Technology, 1997, 144(5):203-208.
Yang, Design of Electrical Capacitance Tomography Sensors, Measurement Science and Technology, 2010, 21(4):042001, 13 pages.
PCT International Search Report and Written Opinion, PCT/US2020/041659, dated Sep. 25, 2020, 6 pages.

\* cited by examiner

SYSTEM AND METHOD FOR IMAGING TENDON CROSS SECTIONS FOR DETECTING VOIDS AND OTHER DEFICIENCIES IN GROUTED EXTERNAL TENDONS

CROSS-REFERENCE TO RELATED APPLICATION

This application is a 371 U.S. National Phase entry of International Application No. PCT/US2020/041659, filed Jul. 10, 2020, which claims the benefit of U.S. Provisional Patent Application No. 62/873,369, filed Jul. 12, 2019, each of which are incorporated herein by reference in their entirety for all purposes.

TECHNICAL FIELD

The present invention is generally related to assessing grout deficiencies within building constructions.

BACKGROUND

Post-tensioned construction is a construction technique in which portions of a structure, such as a bridge, are secured to each other using "tendons" that extend throughout the structure. The tendons comprise an outer duct through which steel strands extend. Once the tendons have been placed into position, the strands are tensioned to provide rigidity to the structure.

In order to prevent corrosion of the steel strands and improve mechanical performance, the ducts are filled with a grout material, which typically comprises a mixture of cement and water. When the grout is properly distributed within the duct, it creates a chemical environment that protects the steel. When the grout is not properly distributed, however, corrosion can occur. For example, if air gaps exist within the duct, the portions of the strands within those portions are exposed and may corrode. Alternatively, if the grout is not mixed properly or the mixture separates, regions that only contain water can be formed, which also can lead to corrosion. Thus, harmful grout issues or conditions in tendons include voids, spots of chalky grout, excessive water content or even free water.

There is currently no economical and reliable method of nondestructive detection of grout deficiency leading to corrosion within external post-tensioned tendon ducts. Corrosion can go undetected until catastrophic failure occurs potentially leading to structural failure, injury or loss of life.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

SUMMARY

Figure 1:
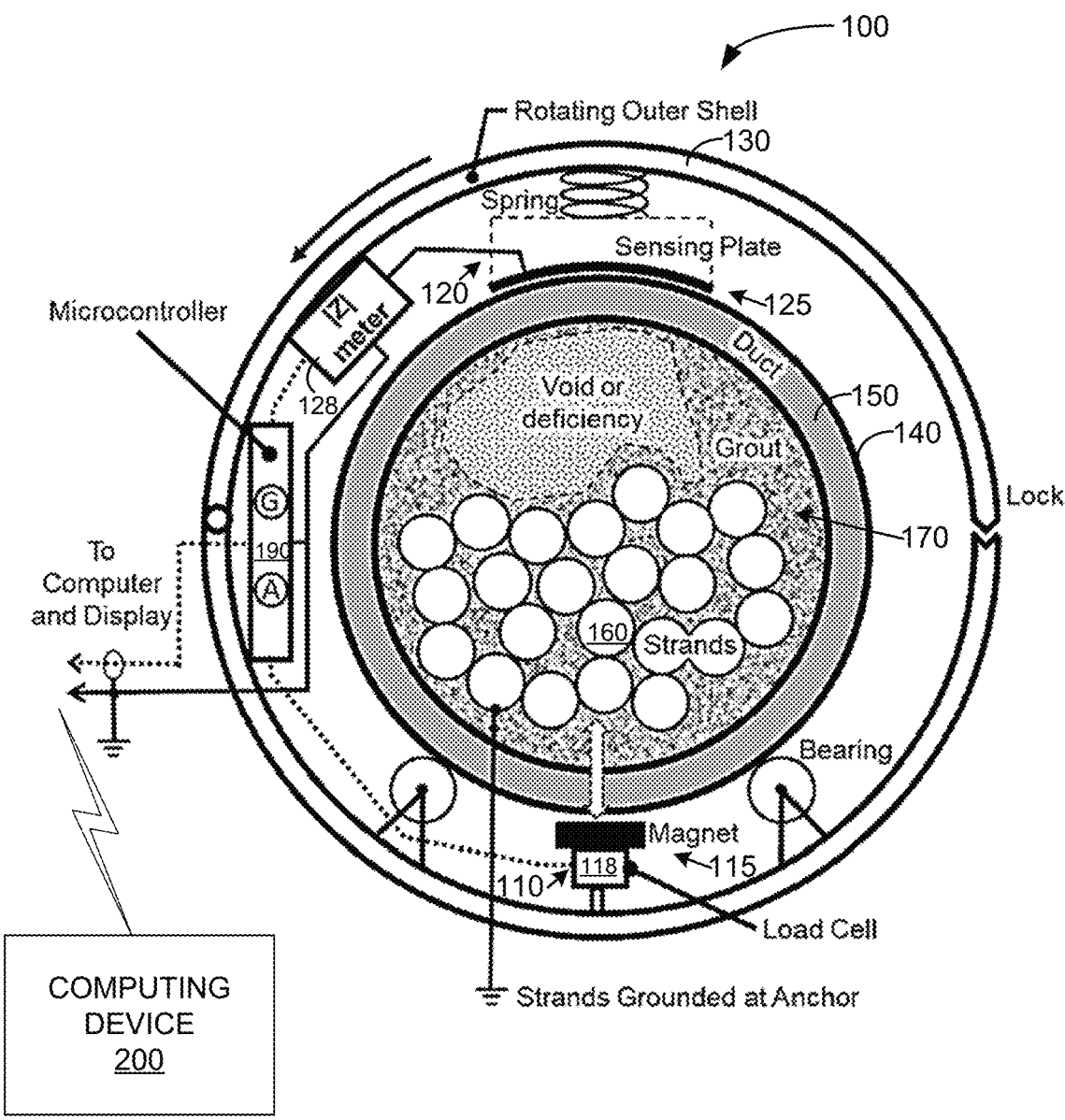
FIG. 1 is an exemplary embodiment of a tendon imaging unit in accordance with various embodiments of the present disclosure.

Aspects of the present disclosure are related to systems and methods for indicating a grout condition within a post-tensioned tendon. In one aspect, among others, such a system comprises a force measuring sensor that provides data indicating magnetic forces applied to a magnet and an impedance sensor that provides measurement data involving an impedance between a metallic sensing plate and metallic strands within the post-tensioned tendon. In the system, a mechanism is adapted to mount to the post-tensioned tendon and position the magnet and the metallic sensing plate in close proximity to an outer surface of the tendon, in which the mechanism is further adapted to facilitate moving of the magnet and the metallic sensing plate around the outer surface of the post-tensioned tendon. Thus, a computing device is configured to generate an image of a cross-section of the post-tensioned tendon indicating one or more grout conditions in spatial proximity to the metallic strands within the post-tensioned tendon based on at least data provided by the impedance sensor and the force measuring sensor.

Aspects of the present disclosure are also related to a method of indicating a grout condition within a post-tensioned tendon. Such a method comprises positioning a magnet and a metallic sensing plate in close proximity to an outer surface of the post-tensioned tendon; rotating the magnet and the metallic sensing plate around the outer surface of the post-tensioned tendon; measuring an amount of magnetic forces applied to the magnet during rotation of the magnet around the post-tensioned tendon; measuring an impedance between the metallic sensing plate and metallic strands within the post-tensioned tendon during rotation of the metallic sensing plate around the post-tensioned tendon; and generating an image of a cross-section of the post-tensioned tendon indicating one or more grout conditions in spatial proximity to the metallic strands within the post-tensioned tendon based on measurement data using the magnet and the metallic sensing plate.

In one or more aspects, grout conditions are identified by a color mapping based on the data provided by the impedance sensor and/or the image is generated by assigning a color-code to impedance measurement data obtained from the metallic sensing plate. In one or more aspects, a first color represents a normal grout condition, a second color represents a full void grout condition, and a third color represents a partial void grout condition. In one or more aspects, a shading of the third color represents a concentration level of water that is partially filling a void in the grout.

In one or more aspects, an angular positioning module tracks positioning of the magnet and the metallic sensing plate as each travels around the outer surface of the post-tensioned tendon. In one or more aspects, positioning of the metallic strands is determined based upon force data supplied by the force measuring sensor and/or a radial plot of the tendon is generated that identifies strand positions. In one or more aspects, the image is generated by deconvoluting magnetic force values to generate a radial plot that provides an indication of a location of the strands within the tendon.

In one or more aspects, the force measuring sensor is a load cell, the mechanism includes a shell member that mounts to the outer surface of the post-tensioned tendon, and/or the magnet and the metallic sensing plate are accommodated at opposite points of a circumference of the shell member.

Other systems, methods, features, and advantages of the present disclosure will be or become apparent to one with skill in the art upon examination of the following drawings and detailed description. It is intended that all such additional systems, methods, features, and advantages be included within this description.

DETAILED DESCRIPTION

The present disclosure describes embodiments of systems and methods for assessing grout deficiencies in building constructions using magnetic and impedance sensing. In some embodiments, a magnet traverses the circumference of the tendon and the force with which it is attracted to the strands within the tendon is measured as a function of angular position. Concurrently, an impedance sensor traverses the circumference of the tendon and measures an electric impedance between the impedance sensor and strands within the tendon. Variations in the electric impedance between the sensor and the strands identify grout deficiencies. The force and impedance information can then be used to create a radial plot that provides an indication of the location of the strands within the tendon and an indication of grout deficiencies within the tendon.

Inadequate grouting has been found to be associated with a corrosion of post tensioning steel in grouted tendons used in bridges, as documented in various notable cases over the last two decades. Grouting deficiencies include voids where bleed water existed and was later reabsorbed elsewhere or evaporated, regions of chalky low strength grout, and regions where excessive water content or even free water is present. In those zones, the mechanical bond between the steel strand and the grout is reduced and, of more concern, the strand steel risks corrosion failure. Given these severe consequences, strict grouting quality guidelines are in place by specifying agencies requiring absence of deficiencies, such as bleed water or voids, although seemingly not widely addressing the degree to which those anomalies may become a statistical reality. Anomalies do develop to some degree and reliable non-destructive testing (NDT) detection of grout anomalies is needed as part of any approach to ensure long term integrity of post-tensioned (PT) bridges.

Nondestructive assessment of a grout condition is thus often needed, preferably by a cross section imaging method. However, such methods tend to be expensive to implement and slow to operate, as well as require health risk management due to the use of penetrating radiation, resulting in limited deployment. Therefore, a non-destructive, rapid, inexpensive, and safe imaging method to detect grout deficiencies as an early indicator of strand corrosion risk, and such is needed and is the objective of the present disclosure.

In accordance with the present disclosure, a magnetic sensing approach to image the position of the steel strand bundle is combined with an electric impedance approach to evaluate the condition of the grout space. Both are embodied in a device that images the tendon's cross section. The magnetic sensor has a magnet and a force measuring transducer/sensor (e.g., load cell) and travels around the circumference of the tendon and measures the force of attraction between the magnet of the sensor and the steel strands, from which an image of the strand pattern inside the tendon is created. For example, the force attraction data is converted into radial position information for the steel strand bundle, producing a base image of the tendon cross section, thus delineating the location of the grout space. Simultaneously, a traveling impedance sensor (e.g., a capacitance plate impedance sensor) rotates around the tendon and measures variations of the electric impedance between the impedance sensor and the strands in the tendon. The impedance variations identify a condition of the grout surrounding the strands in the tendon, such as grout deficiencies. The impedance and strand position data create a complete color-coded image of the tendon cross section indicating or flagging grout deficiencies. In addition to the force and impedance data, an gyroscope/accelerometer device (e.g., an angular positioning module) provides positional data on the sensor assembly, thus providing complementary positional data. Thus, measured changes in magnetic force and impedance values depending on strand position can be acquired by the TIU. The overall information is integrated by computation into a full image of the tendon cross section, mapping on near real time the extent and nature of the grout deficiencies.

Such tools and techniques can serve as an important supplement to regularly scheduled bridge inspections like those under the U.S. Department of Transportation Federal Highway Administration (FHWA) National Bridge Inspection Standards, where for most bridges a routine inspection is required at 24 month intervals. Tendon cross section evaluations could be specified for locations selected on a spot schedule basis in areas previously identified as high risk (e.g., near anchors, high points), but not formerly assessed. Alternatively, or as a supplement, this type of evaluation tool may be applied at unexpected tendon failure events when urgent non-destructive testing imaging information of peer tendons not formerly assessed could help identify other elements at risk. In all instances, the bridge owner receives information on the presence and extent of grout deficiencies that can increase the risk of corrosion of the tendon load bearing components. That knowledge, which may remain uncovered in the absence of a readily deployable method such as presented here, can then be used for adjusting maintenance strategies and their implementation from the standpoint of bridge life cycle needs.

The electrical impedance of grout is a function of its dielectric properties and the ionic conductivity of the pore solution, which are both indicative of the grout condition. Various versions of impedance-related methods, in the form of electric capacitance tomography or of making the grout path as a part of an electronic oscillating circuit, have been proposed as well as deployed in actual practice. However, while those applications identify grout anomalies manifested by changes in dielectric properties or conductivity, information on the spatial relationship between grout anomalies and the steel strand bundle in the form of a cross-sectional visual image is at best quite limited.

The combination of impedance with spatial image information is a powerful enhancement of tendon inspection tools and techniques. For example, interpretation of the significance of a detected grout deficiency may vary depending on whether it is related to a small or to a large grout region in the cross-section space between the strand bundle and the duct wall. Moreover, the spatial information would also serve to refine the processing of the impedance values obtained, because the measured impedance depends not only on grout condition but also on the thickness of the grout zone between the polymer duct wall and the steel strand envelope.

Referring now to FIG. 1, an exemplary embodiment of a tendon imaging unit (TIU) 100 is presented. In one embodiment, a magnetic sensor assembly 110 and an impedance sensor assembly 120 are accommodated at opposite points of a circumference of a rotating shell 130, thereby creating an imaging unit that can slide along successive places on the tendon length. Accordingly, in various embodiments, a mechanism comprising the shell member 130 can be temporality mounted to a tendon 140 in a desired position along its length. As discussed, the tendon 140 includes a duct 150 that surrounds multiple steel strands 160 and grout 170. In the illustrated embodiment, the shell member 130 rotates around the tendon 140.

In one embodiment, a magnet 115 is positioned in a center of an array of four ball-bearing rollers, keeping a nearly steady magnet face to outer duct surface distance of the tendon 140. The presence of the ferromagnetic steel strands 160 in the tendon 140 can produce a measurable attractive force on the magnet 115. By affixing the magnet 115 to a load cell 118 (or other type of force measuring sensor) positioned so that the disk face of the magnet 115 is normal to the radius of the tendon cross section and by keeping the shell assembly 130 at a fixed distance to the external surface of the tendon duct 150, the TIU 100 is configured to measure an amount of attractive force produced by the steel strands 160.

In one embodiment, a sensing plate 125 of the impedance sensor assembly 120 is metallic and may be made of articulated stainless steel elastic segments. The sensing plate 125 can be pressed closely against the surface of the duct 150 by one or more springs in series. At any selected place along the tendon 140, the combined action of a spring, flexible capacitive sensing plate 125 and bearings permitted smooth, hand actuated rotation of the TIU 100 while maintaining steady dimensional positioning of the sensors with respect to the tendon perimeter. Signal conditioning and initial processing can take place on an onboard electronic microcontroller 190, which includes a gyroscope "G" and an accelerometer "A" (that act as an angular positioning module) to keep track of angular position and data to adjust for gravitational and centripetal forces. Further processing can be handled by executable software at a computer 200 connected to the traveling combined TIU unit 100. The resulting images from consecutive places provided a progressive view of the tendon interior flagging grout anomalies.

For the magnetic module 110 and measurements, a disk-shaped permanent magnet 115 (with magnetization normal to the disk face) placed near the external duct surface is operable to provide a magnetic field of sufficient reach into the tendon 140. The presence of the ferromagnetic steel strands 160 in this field produces a measurable attractive force on the magnet 115. The amount of attractive force is greater or smaller if the strand bundle surface was nearer or further respectively away from the magnet 115. The force-distance behavior follows well-established relationships, so the force measurement can be readily converted into a radial distance value. Thus, the magnetic measurements together with the corresponding rotation angle values provided precise information on the location of the strand bundle envelope within a polymer duct 150, creating an image of the bundle inside the duct 150.

In an exemplary embodiment, load cell data (involving the attractive forces produced by the tendon strands 160) can be saved synchronous with a time array. The recorded force values are the result of convolution of the actual force values with the step function response of the magnetic sensor 110—an effect not unlike motion blur in a photograph with a panning camera. To better approximate the actual force values, the measured force data can be corrected by Fourier transform deconvolution in a computer 200, using a separately measured determination of the step response of the magnetic sensor assembly 110.

The electrical impedance (modulus), |Z|, measured by an impedance meter or monitor 128 of the TIU unit 100, is that of the capacitor formed between the metallic sensing plate 125 hugging the external surface of the tendon 140 and the metallic strand assembly inside the tendon 140. The strands 160 are all shorted together by the metallic anchor, which in United States construction is usually connected to bridge ground. The varying impedance values provides an indication of the presence and extent of or absence of grout anomalies as a function of rotation angle. The impedance information (depending on grout condition) may then be used to color-code the space between the duct inner wall and the strand bundle in the image produced by the magnetic sensor assembly 110. The result is a near real-time cross section image of the tendon 140 on the display of the processing computer 200, with grout deficiencies identified by color mapping.

Figure 2A:
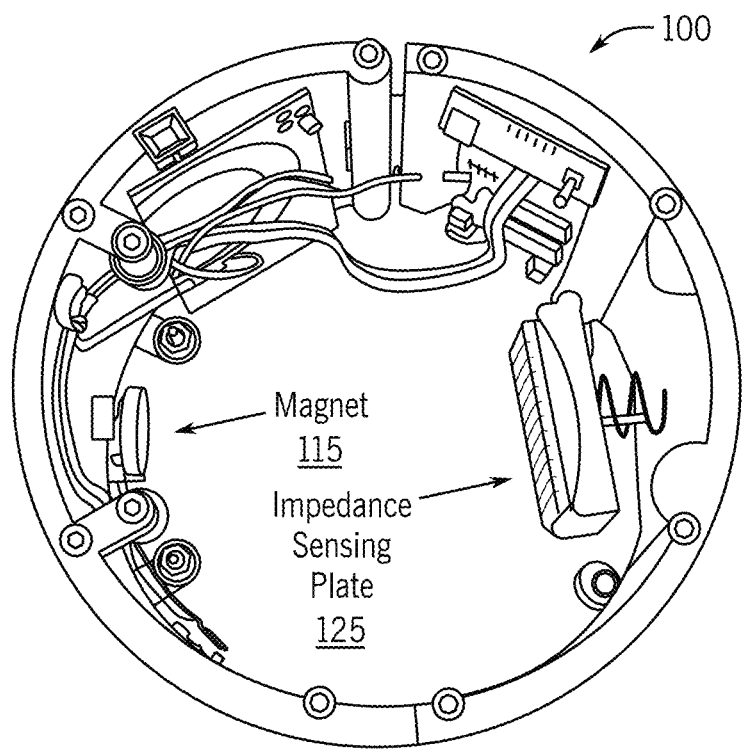
FIGS. 2A-2B shows images of a physical prototype of an exemplary embodiment of a tendon imaging unit in accordance with the present disclosure.
Figure 2B:
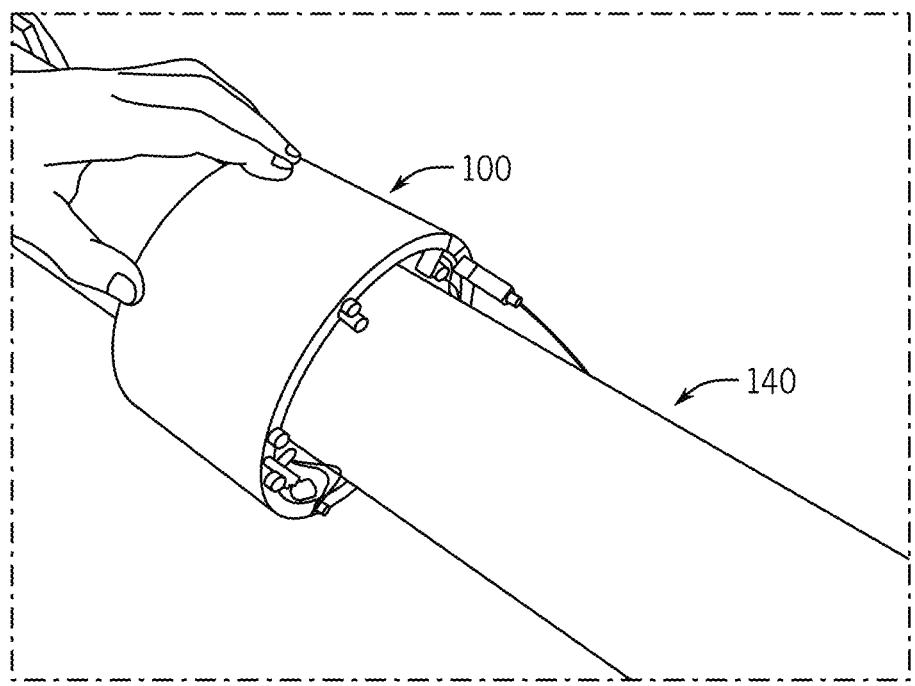

FIGS. 2A-2B shows images of a physical prototype of an exemplary embodiment of the TIU 100. In particular, FIG. 2A provides an axial view of an embodiment of TIU prototype and FIG. 2B shows a placement of the TIU prototype on a 114 mm diameter tendon. The TIU prototype features, but is not limited to only having, a clamshell-mounted unit body 130 having a diameter of ~180 mm and is ~110 mm long. These compact dimensions and resulting small thickness on the tendon radius enabled imaging to extend to tight spots close to other tendons, structural walls, and anchoring or deviation block terminations. For this particular prototype design, a slender data cable reported measurement results to a monitoring and display computer 200. An additional trailing cable connected the impedance circuit ground directly to bridge ground and hence to the strand bundle. From subsequent testing, it was found also that bridge ground may be practically replaced with a metal plate with enough capacitive coupling to the bridge segment floor, or even made unnecessary due to residual capacitive coupling to the surrounding structure via the data cable and the computer 200.

For strand envelope sensing, the sensing magnet 115 of the TIU prototype was tested and determined to have a magnetic moment of ~4 $A \cdot m^2$, resulting in attractive forces to the ferromagnetic strand bundle near ~1N at the closest operating distances. In the prototype, the magnet rode in the center of an array of 4 ball-bearing rollers, keeping a nearly steady magnet face to outer duct surface distance h of ~2 mm. The assembly was observed to tolerate cross section duct ellipticity (ratio of major to minor axes) as high as 1.1 while still maintaining sufficient magnet-duct clearance and providing useable force data.

The measured force data was corrected by Fourier transform deconvolution in a host computer 200, using a separately measured determination of the step response of the sensor. That response was treated in simplified form as an exponential settling with a characteristic time of ~0.065 seconds.

The corrected force information may then be processed to obtain values of the depth of the strand bundle envelope beneath the inner surface of the tendon duct 150, as a function of the angular position within the cross section. For simplicity, it was assumed that there is a power-law dependence $$F_a = k * z^{1/n} \quad \text{(Equation 1)}$$

between the corrected force $F_a$, at a given angular position, and the local distance z at that angular position between the center of the magnet 115 and the edge of the strand envelope, with k as a constant and n as the exponent. It is noted that this treatment considers only the value of the force at a single angular position, so it is only an approximate alternative to an otherwise computationally intensive full deconvolution operation. The results were nevertheless quite useful for the intended purpose. To obtain optimized values of the parameters in Equation 1, the value of k was determined by experimental calibration; while for the more critical value of n (which tends to be large) finite element modeling calculations were performed with different magnet-strand combinations. Those calculations yielded values of k=207 gF-cm$^n$ and n=3.185 as a generic set with a provision for small calibration adjustments in specific TIU builds.

With the parameter values in place, the distance G from the inner duct perimeter to the strand envelope at a given angular position 6 was obtained from the force value $F_a$ there by $$G(\theta) = \left(\frac{k}{F_a(\theta)}\right)^{\frac{1}{n}} - \left(\frac{w}{2} + H + d_D\right) \quad \text{(Equation 2)}$$

where w is the magnet thickness, h is the distance between the magnet face and the external surface of the duct, do is the polymeric duct wall thickness, available from tendon construction data, or spot probing with minimal disruption at a representative location, or as an estimate (e.g., 6 mm) of typical values if precise imaging is not critical. The G(θ) results were then presented in a polar plot format scaled to show the outline of the strand envelope within a circular tendon cross section in the form of a colored silhouette.

For impedance sensing, the assembled capacitive sensing plate 125 (of an exemplary impedance sensor assembly 120) measured 50 mm×50 mm square and was pressed closely against the surface of the duct 150 by a combination of the elastic interconnection of stainless steel elastic segments of the sensing plate 125 and one or more springs of the TIU assembly 100. This construction was robust and durable which allowed the plate 125 to tightly fit during rotation against the duct eliminating intervening air space. Despite that, the construction also minimized friction that would otherwise displace the plate 125 from its intended position, as well as tolerated the minor duct surface scratches and similar irregularities normally present in tendons in the field. Preliminary tests with laboratory tendons evaluated the use of AC frequencies ranging from 0.1 MHz to 10 MHz to measure the impedance behavior of various tendon cross-sections. Based on the results an operating frequency of 1 MHz was chosen, which provided a practical working compromise between adequate sensitivity to grout space property variations and simplicity of implementation.

For the present TIU assembly 100, the high frequency electrical behavior of the system for a given angular position of the impedance sensor assembly 120 was abstracted as being that of a simple parallel-plate capacitor with a layered dielectric/conductive fill space. The curvature and unevenness of the plate, tendon cross section, and strand bundle surface were ignored, as were any non-uniform current distribution effects. Also, by operating at a high enough frequency the impedances of intervening interfaces were considered to be negligible so the measured impedance Z was here simplified as $$Z = Z_D + Z_G \quad \text{(Equation 3)}$$

where $Z_D$ and $Z_G$ are the duct layer and grout space impedances, respectively.

As the duct material is normally quite uniform in composition and thickness ($d_D$), the impedance component $Z_D$ was regarded as being approximately the same at all angles so variations in the measured value of Z reflected mainly variations in $Z_G$. $Z_G$ depends on the local grout space thickness $d_G$ and on the grout composite condition. The thickness dependence can be factored out if necessary, using the knowledge of the strand envelope position at each angle provided by the magnetic measurements. After accounting for thickness, variations in the value $Z_G$ (and thus Z) serve as indicators of deficiency as shown next.

The grout space is normally filled with sound hydrated grout, or otherwise by a composite mixture of some proportion of sound hydrated grout and deficient space. The deficient portion include a void or voids filled with air or some water solution, unhydrated or partially hydrated grout, or so-called soft or chalky grout with a high water to grout powder ratio. Sound, deficiency-free grout behaves at a given test frequency f as a material with an effective electric conductivity $\sigma_G$ and dielectric constant $\varepsilon_G$. Thus, the impedance of a notional grout space with effective area A and depth $d_G$ is inversely proportional to the combination of those properties, as in a "leaky capacitor" analog:

$$Z_G = \frac{d_G}{A * (j * 2 * \pi * f * \varepsilon_0 * \varepsilon_G + \sigma_G)} \quad \text{(Equation 4)}$$

where $\varepsilon_0$ is the permittivity of vacuum=8.85×10$^{-12}$ F·m$^{-1}$ and j=$\sqrt{-1}$.

If the grout space incorporates deficiencies, it may still be viewed on first approximation as a uniform medium having effective values of $\sigma_G$ and $\varepsilon_G$, but different from those for sound grout. For a given grout pore structure both properties tend to increase in value with increasing water content in the pores because of the greater degree of electric pore interconnection, as well as the high dielectric constant of water causing a lower impedance value than that of sound grout. If the pore structure is more open due to a local excess of mixing water (a "soft" grout), the impedance decrease may be even more pronounced. A void filled with water, especially if it is highly conductive as in bleed water, would represent an extremely low grout impedance case. If the deficiencies consist instead of air-filled voids, it may be expected that as the fraction of affected space approaches unity (a "full void"), $\sigma_G$ would tend to 0 and $\varepsilon_G$ to 1, resulting in a markedly higher impedance than that of sound grout. Correspondingly for deficiencies consisting of unhydrated grout, those parameters would tend to be intermediate between the cases of full air voids and sound grout. Therefore, the value of $Z_G$ and its variations can provide an important indicator of the presence and extent of grout deficiencies. Per the form of Eq. 4, $Z_G$ may be normalized by division by the value of do thus focusing only on the deficiency-sensitive property changes. As it will be shown, changes in grout properties alone were in many cases dominant, so for practical implementation grout space thickness normalization was not built in the data processing algorithms. That choice was not limiting, however, and it can be readily implemented in various embodiments.

For simplicity of operation and given that $Z_D$ is nearly 267 constant, variations in the value of the total impedance Z (rather than of $Z_G$ which would have required additional processing) were used as the main indicator of deficiencies. Impedance values are complex numbers with a reactive (imaginary) and a resistive (real) part, and separate evaluation of those components has the potential of being more revealing of the nature and extent of the deficiencies. However, precise separation is instrumentally demanding and previous tests have shown that grout anomalies were sufficiently revealed by changes in the modulus of the impedance, here designated as |Z|. That value, which is equal to the quadratic combination of both parts, is less costly to implement instrumentally with the necessary accuracy and it was adopted as the detection parameter for the TIU 100. Thus, the impedance sensor assembly 120 produced a time-synchronized |Z|(θ) data stream that was sent to a processing unit or computer simultaneously with the force load data from the magnetic sensor assembly 110.

In accordance with various embodiments of the present disclosure, the impedance indication of grout condition together with the strand position information, may then be combined into a color-coded 2D image of the cross section indicating or flagging grout deficiencies and spatial context. For operation, rotating the ring one full turn around the tendon 140 produced simultaneously 360° angular profiles of the magnetic force and impedance modulus, which were registered to correspond to the values for coincident angular positions and stored in a data file on the monitoring and display computer 200. Impedance and angular position data acquisition rate was 10 Hz. From there the data was filtered, conditioned, and processed in order to generate the cross-sectional image of the tendon 140. Typically, a full rotation scan and associated image display was completed in only 10 seconds. The procedure yielded a set of less than 100 data points that were properly parsed based on the gyroscope readings, so that the displayed pattern was nearly insensitive to variations in rotation speed that may have taken place during the image acquisition. Furthermore, a calibration procedure was developed for field applications as discussed later on.

Notably, the entire unit and housing of the TIU prototype (FIGS. 2A-2B) was made with readily available components and ordinary 3D printing equipment. Thus, the TIU prototype can be quickly and inexpensively replicated if multiple units need to be deployed at a field site for either routine or emergency assessment. Such deployment is further facilitated by simplicity of operation that does not require specialized personnel, has compact dimensions, and a fast display of results.

A first set of experiments, used for development of a magnetic strand location method, was conducted with the central region of five legacy tendon segments from a prior investigation. The ~0.30 m tendon segments had an 89 mm external diameter high-density polyethylene (HDPE) of 5.5 mm wall thickness. The tendons had twelve ASTM A416 12.7 mm nominal diameter size, 7-wire formerly stressed steel strands fully embedded in QPL-938 Masterflow® 1341 grout which had no significant magnetic susceptibility. During construction, the strands were evenly distributed at the anchor ends, but placement within the cross section of the tendon segments tested varied from even to strongly lop-sided depending on their proximity to a deviation block bend. An early developmental magnetic imaging-only version of the TIU prototype was used for those tests.

Figure 3A:
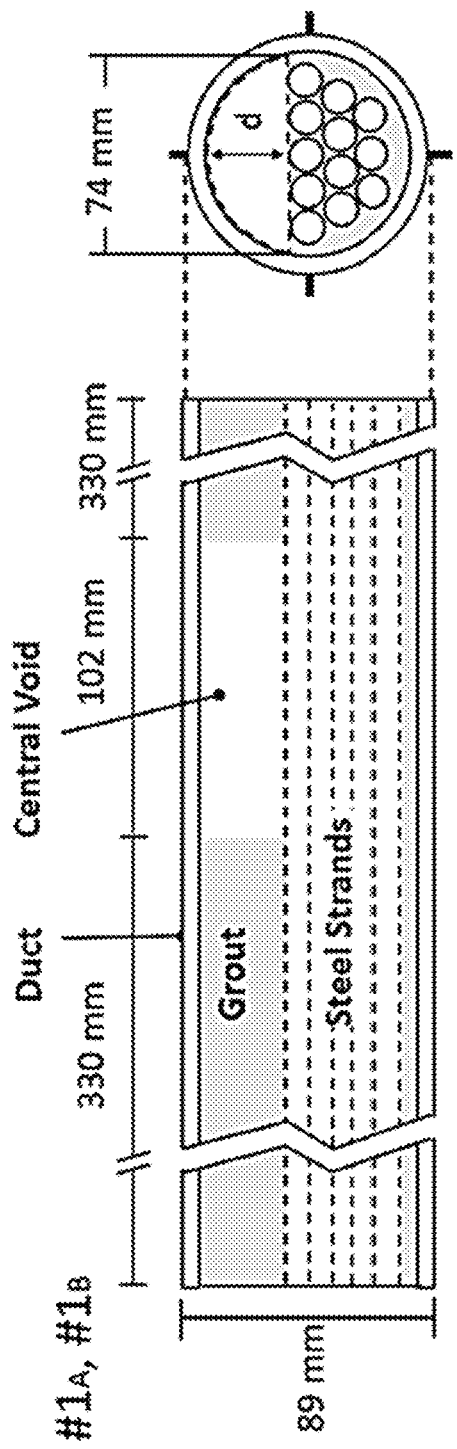
FIGS. 3A-3B show tendon specimen testing layouts for various grout conditions in accordance with the present disclosure.
Figure 3B:
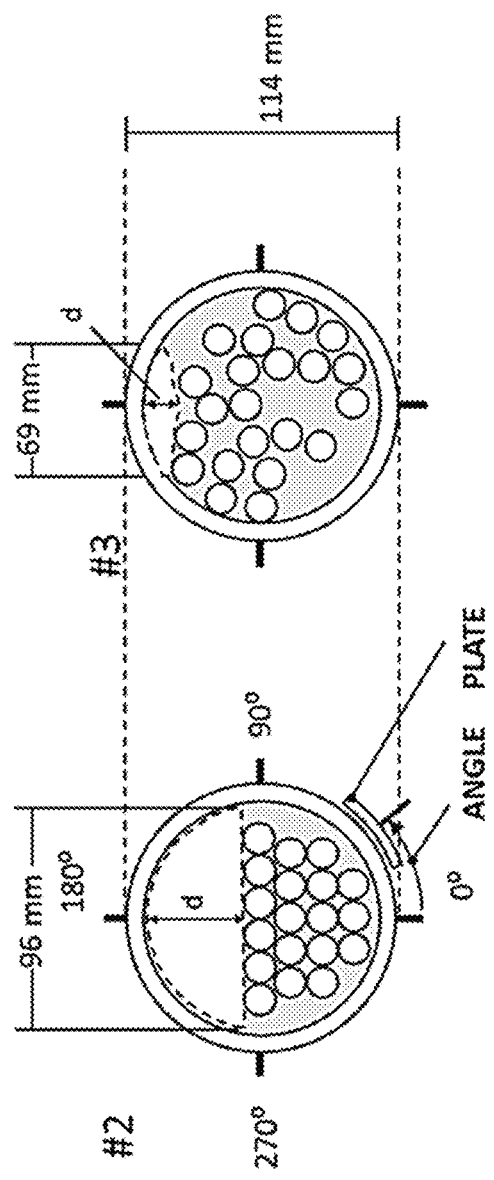

The main laboratory evaluation of the combined magnetic-impedance imaging approach was conducted with tendon segment specimens ranging from 89 mm to 114 mm nominal diameters. FIGS. 3A-3B shows the specimen layouts for four specimens labeled #1A, #1B, #2, and #3. Each of the #1A, #1B, and #2 specimens shared longitudinal dimensions and central void position. Depth dimension d for a central void measures 30 mm, 35 mm, and ~13 mm for #1A/#1B, #2, and #3 respectively. Plate angle reference and orientation, illustrated for #2, was common in all tests.

The smaller diameter specimens (#1A and #1B in FIG. 3A) with a ~5.6 mm HDPE thickness were a set of two replicates, each ~0.76 m long, that contained twelve unstressed ASTM A416 12.7 mm nominal diameter size, 7-wire steel strands lumped away from the center with a 102 mm long central void with a volume of ~215,000 mm³.

One of the 114 mm diameter specimens (#2 in FIG. 3B), with a ~7 mm HDPE thickness, was a ~0.76 m long laboratory sample that contained nineteen 12.7 mm steel strands lumped away from the center with a 102 mm long void similar to that in the smaller diameter tendons, with a volume of ~300 mL.

The other 114 mm diameter specimen (#3 in FIG. 3B) was extracted from the John Ringling Causeway Bridge, that had experienced strand corrosion incidents. The segment was 1.55 m long with twenty-four 12.7 mm strands and a HDPE thickness of ~7 mm. The segment had no recognizable native grout deficiencies, so a ~100 mm long grout void, centered ~300 mm from one end, was chiseled in the lab. That void had a volume of ~80 mL reaching from the inner surface of the duct 150 to the strand envelope.

The voids in the laboratory tendons were created by placing a polystyrene foam insert of the desired approximate dimensions in the mold before casting the grout. After curing, the foam was dissolved by inserting a small amount of acetone via a small hole in the duct wall. The acetone then evaporated leaving a solid residue with volume only ~1% of that of the initial insert, and a full void of nearly the same size as the insert. The duct wall hole, re-sealable with a polymeric plug, allowed for temporary insertion and removal of alternative void fillings that included unhydrated grout and water (for the smaller diameter tendons), without substantially affecting the condition of the rest of the tendon segment. For the bridge tendon segment, the grout was first exposed by cutting out a ~70 mm by ~100 mm rectangle of the duct 150, which was afterwards reattached at the edges with an epoxy compound, leaving a smooth external surface over and around the void. The approximately greatest depth of each void, d, is shown in FIGS. 3A-3B as well.

Specimens (#1A, #1B, and #2) were cast with the EUCO Cable Grout PTX product, with a water to grout ratio of 0.23, as recommended per manufacture's specifications (EUCO 2017). This material had noticeably magnetic susceptibility, with effects discussed later on. Evaluations were conducted at curing ages ranging from ~5 months to ~2 years. The hydrated grout had a density of ~2.0 g/cm3, and resistivity in the order of 100,000 ohm-cm at the age ~193 days of the imaging evaluations. Angular coordinates used are shown in FIGS. 3A-3B. For a point in the inner wall of the duct 150, the voids spanned an angular range of somewhat <~180° for the laboratory tendons, and <~90° for the field tendon. All tests were conducted using the TIU prototype of FIGS. 2A-2B, at laboratory ambient temperature (~22° C.), and included the following conditions and testing setups.

To evaluate a sound/normal grout condition, the rotating TIU unit 100 was centered on an axial position on the tendons 140 halfway between the edge of the central void and the end of the tendon. Thus, the magnetic and impedance sensors were centered on a sound grout region ~1.5 tendon duct diameters clear from any variation. For the field tendon, the TIU unit 100 was centered on tendon axis point ~300 m away from the edge of the void region, with a clear sound region >3 tendon duct diameters.

For a grout condition having an air-filled void (as indicated in FIGS. 3A-3B), image acquisition was performed with the TIU unit 100 positioned on the center of each of the pictured voids and for all specimens. For a grout condition having a filled void space, the void space was filled with unhydrated dry grout powder, simulating an unmixed grout plug extreme condition sent into the tendon. The unhydrated powder had a density of 1.2 $g/cm^3$. This condition was examined with the #1A and #1B replicate specimens, in which the powder was removed from the void after completion of testing. For a grout condition having a void filled with diluted water, the void space was filled with a mildly alkaline water solution with pH (as determined with pH color-indicating paper) ranging from 8 to 10 depending on prior condition of the void space. This solution was created by inserting deionized water in the cavity and allowing interaction for ~15 minutes with the grout at the cavity walls or residual unhydrated grout particles from a previous test condition. The condition explored the ability of detecting the outcome of an extreme water segregation event during grout preparation, which would have resulted in only minor ionic species presence. This condition was examined with the #1A and #1B replicate specimens and testing was conducted 15 minutes after introduction of water into the void, after which the water was drained from the void after completion of testing. For a grout condition having a void filled with concentrated water, the void space was filled with a highly alkaline NaOH water solution (pH~13.5, ~0.3M NaOH, resistivity ~20 Ω-cm). This solution is a simplified analog of the pore water often encountered in cementitious systems, where K and Na cations create a highly alkaline mixture with high electric conductivity. The condition may resemble a void filled with bleed water or similar high ionic content liquid segregation that took the place of otherwise sound grout. Examined only with the #1A and #1B replicate specimens; tests conducted 15 minutes after introduction of solution into the void, after which the solution was drained away. This condition was evaluated after the Dilute Water tests.

To ensure that no air gap remained in the cavity when a condition was being introduced certain precautions were taken. For the unhydrated (UH) grout condition, the powder was compacted, and the tendon specimen was vibrated and tapped with a mallet. For the water conditions, the specimens were only vibrated and tapped, and the cavity was allowed to overflow and then dried with a towel paper to make sure the polymer duct was dry.

Figure 4:
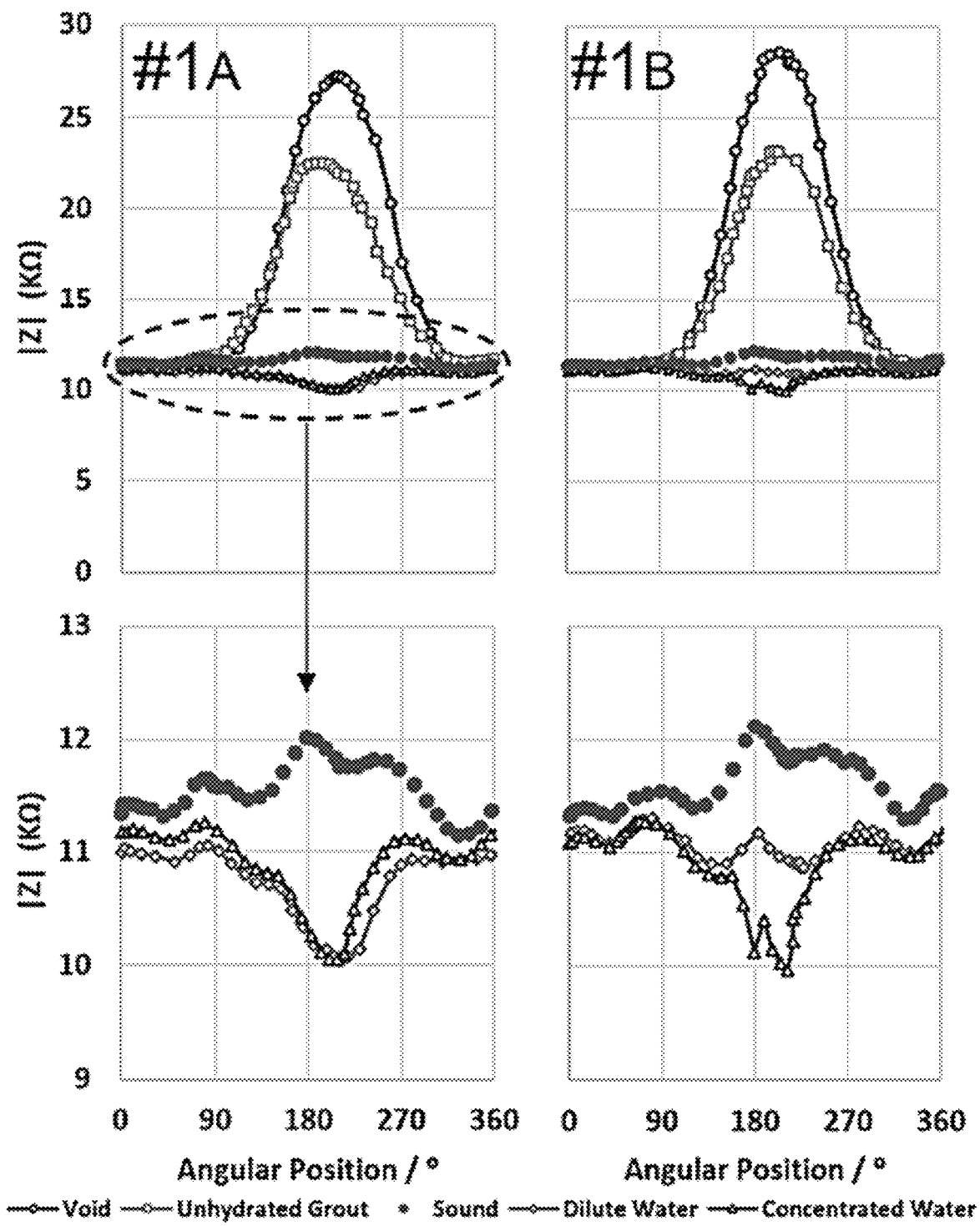
FIG. 4 shows graphs depicting a modulus of impedance in kΩ versus angular position for the tendon specimen layouts of FIG. 3A for sound grout conditions (top) and the grout condition involving water-filled voids (bottom) in accordance with the present disclosure.

Overall trends of impedance measurements and reproducibility are illustrated in FIG. 4 for the results from replicate specimens #1A (on left side of figure) and #1B (on the right side of figure). There, the impedance modulus |Z| is shown as a function of angular position of the sensing plate center with 180° corresponding to the apex where the thickest grout space, or alternatively the highest void space is located per FIGS. 3A-3B. Trends were generally the same in the replicate specimens, attesting to reproducibility of the technique and findings. Variation in one case (Dilute Water) was ascribed to test sequencing differences. Additional tests, not shown in the figures, consisted of immediately consecutive measurements for each condition and specimen (including as well specimens #2 and #3) so as to assess repeatability. It was evaluated as the root mean square relative difference (in percent) between the impedances measured in the consecutive tests, computed at regular interpolated intervals over 360°. Results ranged from 0.28% to 5.35%, with 1.68% on average. Those indications of data stability were deemed sufficient for useful application of the tendon imaging method in the conditions evaluated here.

For the sound grout condition, the impedance modulus |Z| varied modestly around the duct perimeter, with only a faint maximum near 180°. This is as expected since the dominant impedance is that of the duct wall, which is nearly constant around the tendon. |Z| for the wall is of significantly higher value (in the order of 10 kΩ for the frequency, duct wall thickness, HDPE dielectric constant, and plate dimensions used) than that of the sound grout space (about 1 order of magnitude smaller). The combination of those estimated values is also in good agreement with the experimental observation. The maximum is more visible in the magnified plots shown in the lower part of FIG. 4 and reflects the grout space at 180° being about 3 times greater than near 0°, due to the crowding of the strands 160 near the bottom.

Much stronger detection differentiation was obtained for the Void condition. In both specimens, there was a pronounced maximum in |Z| near 180°, to about two to three times the value at the opposite end of the perimeter (~0°) where only sound grout is present. The value of |Z| at 0° was nearly the same as for the sound condition when it existed over the entire perimeter. The impedance maximum was moderately shifted in both specimens from an ideal 180° angle. This behavior, confirmed in repeat tests, likely reflected some degree of specimen construction deviation on void forming and casting.

The Unhydrated Grout condition resulted also in a strong differentiation from the Sound case, with a marked maximum near 180°, about ⅔ of the magnitude observed with the full Void condition. The high impedance of the unhydrated grout with respect to that of the sound, hydrated grout was to be expected on various considerations. The amount of cementitious mass per unit volume is expected to be significantly less than that of hydrated grout due to the granular structure without fluid accommodation assistance, so any dielectric behavior inherent to the cementitious components should be correspondingly reduced. Importantly, the high dielectric contribution from the presence of water is absent in unhydrated grout, and electrolytic conductivity is also absent without the presence of water. Thus, the impedance of unhydrated grout should be that of a non-conducting granular material with effective average dielectric constant only modestly higher than that of air. The overall effect was impedance modulus values in between those of sound grout and a full void, somewhat closer to the latter, and in any event clearly detectable.

The Concentrated Water (CW) fill condition yielded impedance values near 180° that were moderately but consistently lower than those of sound grout in the same region, as shown in the enlarged bottom graphs of FIG. 4. This differentiation reflected the high dielectric constant of water (near 80 compared to a value ~ one order of magnitude lower for sound grout), combined with strong ionic conductivity from the ~0.3 M dissolved NaOH. Those factors markedly lowered the impedance of the filled space compared to that of sound grout, resulting in the dip measured near 180°. It is noted that the water closely filled the entire void space, leaving no significant gap near the inner duct surface and therefore allowing for the presence of the highly permittivity/conductive medium to be manifested in the measured impedance changes. The overall relative effect, however, is limited, because of the constant presence of the duct wall and its high series impedance component. Consequently, unlike the cases of the void (V) or unhydrated (UH) grout, the change is only in the order of 10% to 20% of the sound grout case total impedance, so sensitivity to the presence of the simulated bleed water is accordingly only moderate. The impedance response for the lower, normal grout portion of the specimen was, as expected and as in the other cases, much closer to that encountered for the same region in the Sound condition.

The response to the Dilute Water (DW) condition was in one of the replicate test specimens (#1A) quite close to that for the concentrated water, while for #1B it was somewhat intermediate between the Sound and the Concentrated Water conditions. This behavior is consistent with the circumstance that #1A was tested immediately after completing the unhydrated grout tests. Interaction with residual grout particles elevated the solution pH (to~10), evidencing ionic enrichment and corresponding decrease in solution resistivity and lower impedance of the intervening space. In contrast, water introduction in specimen #1B took place at a time when the inner space had experienced prior flushing, resulting in only a mildly alkaline solution (pH ~8). Thus, only the impedance decrease associated with the high dielectric constant of water appears to have been of importance. That dielectric effect although diminished was still evident when contrasted with the Sound grout condition, so the impedance measurements showed reasonable potential for detection of a free water condition even when ionic content was minor.

Specimens #2 and #3 where evaluated only in the Sound and Void conditions, with results of comparable pattern and magnitude to those documented for #1A and #1B. Overall, the impedance measurements were consistent with anticipated behavior and supported the use of that variable as a useful indicator of grout condition for the imaging application intended.

Figure 5:
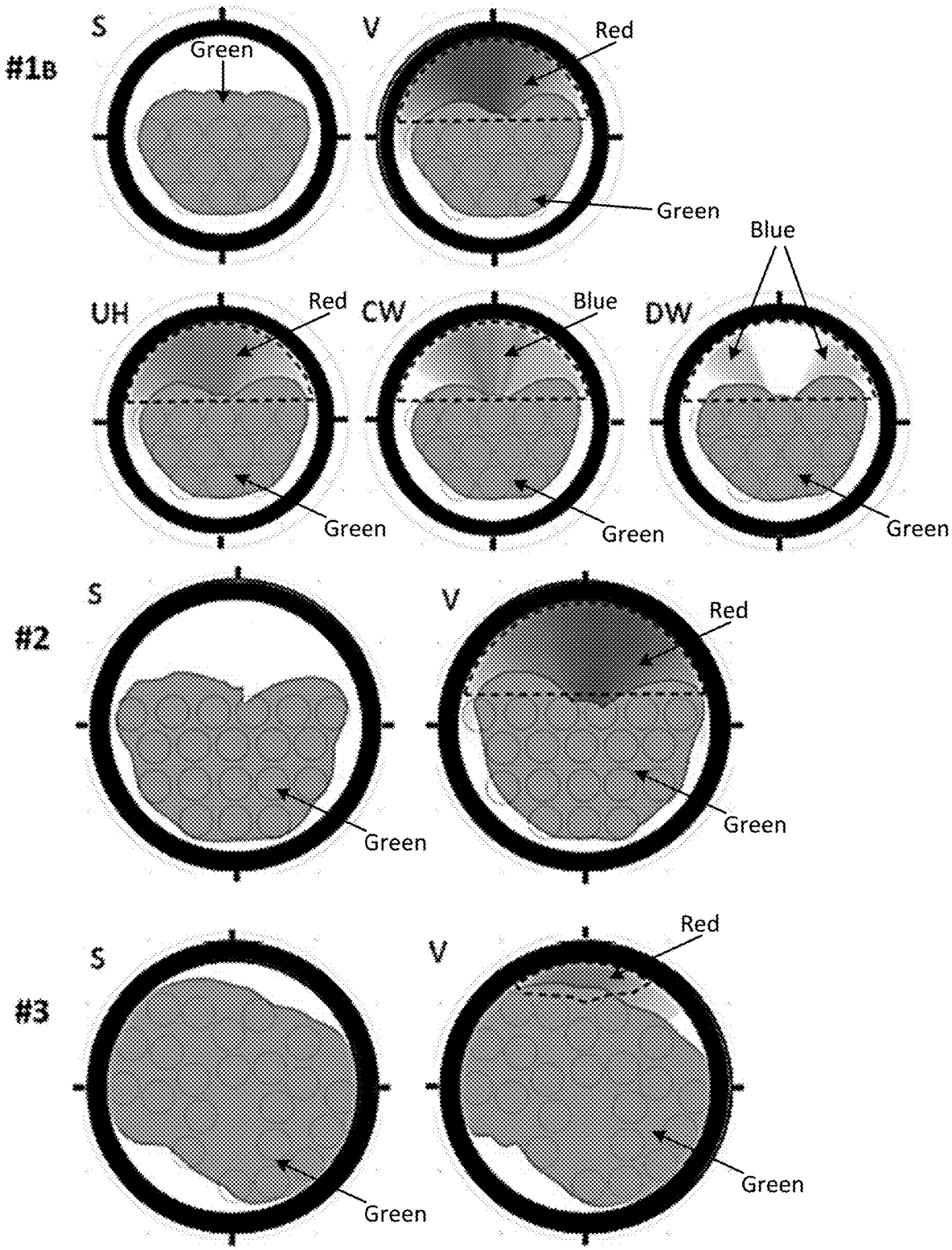
FIG. 5 shows images produced by an exemplary tendon imaging unit of specimens of FIGS. 3A-3B in accordance with various embodiments of the present disclosure.

The cross-sectional image display generated by the TIU 100 is exemplified by the patterns in FIG. 5. Please note that dashed and dotted lines were added for reference to show where voids and individual strands were present in the specimens. In the figure, the outer black ring in the images was scaled to correspond to the actual dimensions of the polymer duct 150. At each rotation angle, the radius line from the center to the inner part of the polymer duct 150 was divided into two segments. The inner region, colored green extended from the center of the duct 150 to the steel strand envelope, which was located at each angle at the radius value determined by the magnetic sensing technique described previously. The outer segment extended from the strand envelope radius until the inner surface of the duct 150. That segment was colored white for an impedance value at that angle indicative of a fully sound grout condition (S), solid red for a full void indication (V), or solid blue for indication of a highly conductive medium such as bleed water. Intermediate impedance values that would be obtained between full void or fully sound grout indications, such as the case a partial void or the transition between a void and sound grout, received a correspondingly intermediate shade between red and white. Conversely, intermediate conditions where impedance decreased with respect to that of sound grout, for example highly dilute water (DW), or grout with a high water/grout ratio (CW), received a corresponding shade between blue and white. Graphically joining the radial segments into a polar diagram created the displayed image of the cross section with visual flagging of grout deficiencies and their character and extent.

For appropriate mapping with reasonable noise rejection and simplicity of interpretation, a calibration and proportioning procedure was established, aimed to field operation. Calibration is ideally performed when having access to a portion of the tendon 140 to be assessed, or of a tendon representative of a population of similarly constructed peer tendons, having a reasonable expectation of containing grout absent of deficiencies. In that case, the TIU 100 is placed on the tendon 140 and an angular impedance profile is obtained. That profile is anticipated to show only modest variation, exemplified by the data for the Sound condition in FIG. 4. For simplicity that variation is ignored and the average value of |Z| over the 360° interval is computed and used as the impedance value descriptive of the sound ground condition. Proportional deviations from that value above and below representative of void and water conditions respectively are then assigned based on the variations observed in the laboratory specimens, and then used to assign colors. The assignment limits can be readily changed in the processing software via a suitable graphical user interface.

The result of the above tests and processing was a highly-descriptive visualization of the inside cross section of the tendon 140 with identification of grouting anomalies. The top part of FIG. 5 displays the results obtained with Specimen #1B, clearly differentiating the conditions discussed in the previous section, and in the context of the position relative to the strand presence in the cross section. It should be recalled that, as stated earlier, differentiation was less precise for grouting issues that resulted in lowered impedance relative to that of sound grout. Similar graphs for Specimen #1B adequately flagged the presence of water but showed similarly strong color intensity for both the dilute and the conductive variations. The lower part of FIG. 5 shows the results for the larger diameter tendon samples #2 and #3. There the position and presence of a full void was also successfully identified in both cases, even in the case of the actual bridge tendon (#3) when the void was associated with a relatively small grout space thickness. Alternative display modes of the same information can be used as well. The outer radial segment was divided into two parts, with the inner part white. For a void indication, the part closest to the duct wall was colored solid red and occupied a fraction of the outer radial segment length proportional to how much a full void condition was approached. For an elevated grout conduction condition, a complementary solid blue scheme applied. The result was a faux designation of anomaly position (always close to the duct wall) but with a bold color pattern for easier flagging of marginal cases.

It is noted that the TIU 100 consistently recovered the general shape and dimensions of the strand bundle envelope, as can be seen by comparison with the actual strand placement. Some deviations from precise recovery existed, mainly in the laboratory specimens, whereby the size of the bundle was modestly overestimated at angular positions further removed from the duct wall. This deviation has been ascribed to the relatively high magnetic permeability of the grout used to prepare the tendon samples, which resulted in a minor increase in the magnetic force on the sensing magnet 115 with consequent underestimation of the strand-magnet distance. Similar effects have been noted in rebar location sensors when working with certain cementitious materials and corrective formulas to minimize this source of strand position uncertainty were developed. These corrections can be approximated by a minor flat amount subtraction from the magnetic force measured as used in Equation 2 and were implemented in TIU processing software, in various embodiments.

Based on comparative analysis, an exemplary tendon imaging unit 100 detects full and outer voids within sample tendons providing comparable results to those of Gamma Ray Tomography but with minimum operator requirements, minimum equipment cost, and minimal health risks. For field demonstration, a prototype TIU 100 was deployed to the John Ringling Causeway Bridge in Sarasota, Fla. and tested on two external field tendons. Prior repairs had replaced other tendons in the bridge that had clear signs of distress, so based on that and based on previous testing, the remaining tendons were deemed not likely to have severe grout deficiencies. Consistent with that expectation, the TIU 100 identified only normal grout there. The tests nevertheless demonstrated the ability of the TIU 100 to obtain reliable and repeatable cross-sectional images of the tested tendons, with clear differentiation of strand envelope patterns. Ease of operation by non-specialist personnel with minimal training, and ability to provide nearly instantaneous images in a field setting by a robust unit with no breakdowns, were demonstrated as well. Such an approach represents a desirable balance between sophistication and equipment/operation costs. Thus, in practical circumstances, systems and methods of the present disclosure can make timely assessment of a large inventory of tendons in a bridge possible, where application of other technologies could have been prohibitively expensive and slow, or limited to only a small selection of tendons.

In accordance with the present disclosure, various systems and methods for imaging grout deficiencies in external tendons have been presented. In various embodiments, magnetic measurements are used to image the strand bundle and impedance measurements are used to identify grout deficiencies in the space between the strand bundle and the tendon duct 150. In an exemplary system or apparatus, magnetic and impedance sensors are physically integrated in a tendon imaging unit 100 (via impedance sensor assembly 120) that is suitable for field measurements in actual bridge tendons 140. From magnetic and impedance measurements, an exemplary TIU system can recover a strand bundle envelope and indications of grout conditions in a non-intrusive manner. As such, in an exemplary embodiment, the TIU 100 can produce a color-coded image of the tendon cross section rapidly displaying the position of the strand bundle, detecting voids, and displaying a condition of the grout 170 within the tendon enclosure based on a combination of the impedance data with the strand position information (obtained from magnetic attraction force measurements). These types of images of the cross section of external post tensioned tendons used in highway bridges can reveal grouting deficiencies that could possibly cause corrosion of the tendon steel strands and may lead to eventual failure of those critical components, if not corrected. It is important to detect deficiencies during inspection of existing bridges, and if possible during the construction phase to enable early remedial measures.

It should be emphasized that the above-described embodiments of the present disclosure are merely possible examples of implementations, merely set forth for a clear understanding of the principles of the disclosure. Many variations and modifications may be made to the above-described embodiment(s) without departing substantially from the principles of the disclosure. All such modifications and variations are intended to be included herein within the scope of this disclosure and protected by the following claims.

The invention claimed is:

1. A system for indicating a grout condition within a post-tensioned tendon, the system comprising:
   a force measuring sensor that provides data indicating magnetic forces applied to a magnet;
   an impedance sensor that provides measurement data involving an impedance between a metallic sensing plate and metallic strands within the post-tensioned tendon;
   a mechanism adapted to mount to the post-tensioned tendon and position the magnet and the metallic sensing plate in close proximity to an outer surface of the tendon, the mechanism further being adapted to facilitate moving of the magnet and the metallic sensing plate around the outer surface of the post-tensioned tendon; and
   a computing device that is configured to generate an image of a cross-section of the post-tensioned tendon indicating one or more grout conditions in spatial proximity to the metallic strands within the post-tensioned tendon based on at least data provided by the impedance sensor and the force measuring sensor.

2. The system of claim 1, wherein grout conditions are identified by a color mapping based on the data provided by the impedance sensor.

3. The system of claim 2, wherein a first color represents a normal grout condition, a second color represents a full void grout condition, and a third color represents a partial void grout condition.

4. The system of claim 3, wherein a shading of the third color represents a concentration level of water that is partially filling a void in grout material.

5. The system of claim 1, further comprising an angular positioning module that tracks positioning of the magnet and the metallic sensing plate as each travels around the outer surface of the post-tensioned tendon.

6. The system of claim 1, wherein the force measuring sensor is a load cell.

7. The system of claim 1, wherein the mechanism includes a shell member that mounts to the tendon.

8. The system of claim 7, wherein the magnet and the metallic sensing plate are accommodated at opposite points of a circumference of the shell member.

9. The system of claim 1, wherein the computing device is configured to determine positioning of the metallic strands based upon force data supplied by the force measuring sensor.

10. The system of claim 9, wherein the computing device is configured to generate a radial plot of the tendon that identifies strand positions.

11. A method of indicating a grout condition within a post-tensioned tendon, the method comprising:
    positioning a magnet and a metallic sensing plate in close proximity to an outer surface of the post-tensioned tendon;
    rotating the magnet and the metallic sensing plate around the outer surface of the post-tensioned tendon;
    measuring an amount of magnetic forces applied to the magnet during rotation of the magnet around the post-tensioned tendon;
    measuring an impedance between the metallic sensing plate and metallic strands within the post-tensioned tendon during rotation of the metallic sensing plate around the post-tensioned tendon; and generating an image of a cross-section of the post-tensioned tendon indicating one or more grout conditions in spatial proximity to the metallic strands within the post-tensioned tendon based on measurement data using the magnet and the metallic sensing plate.

12. The method of claim 11, wherein the image is generated by deconvoluting magnetic force values to generate a radial plot that provides an indication of a location of the strands within the tendon.

13. The method of claim 12, wherein the image is generated by assigning a color-code to impedance measurement data obtained from the metallic sensing plate.

14. The method of claim 13, wherein a first color represents a normal grout condition, a second color represents a full void grout condition, and a third color represents a partial void grout condition.

15. The method of claim 14, wherein a shading of the third color represents a concentration level of water that is partially filling the void in grout material.

16. The method of claim 11, further comprising tracking positioning of the magnet and the metallic sensing plate as each travels around the outer surface of the post-tensioned tendon.

17. The method of claim 11, further comprising mounting the magnet and the metallic sensing plate to the outer surface of the post-tensioned tendon.

18. The method of claim 17, wherein the magnet and the metallic sensing plate are integrated within a shell member that mounts to the post-tensioned tendon.

19. The method of claim 18, wherein the magnet and the metallic sensing plate are accommodated at opposite points of a circumference of the shell member.

20. The method of claim 11, further comprising determining positioning of the strands based upon force data involving the magnet.

* * * * *